(12) United States Patent
Torres

(10) Patent No.: US 9,968,702 B2
(45) Date of Patent: May 15, 2018

(54) AIR FRESHENER

(71) Applicant: L & D S.A.U., Huercal de Almeria (ES)

(72) Inventor: David Fernandez Torres, Huercal de Almeria (ES)

(73) Assignee: L & D S.A.U., Huercal de Almeria (ES)

( * ) Notice: Subject to any disclaimer, the term of this patent is extended or adjusted under 35 U.S.C. 154(b) by 171 days.

(21) Appl. No.: 14/651,679

(22) PCT Filed: Jan. 10, 2013

(86) PCT No.: PCT/ES2013/000008
§ 371 (c)(1),
(2) Date: Jun. 12, 2015

(87) PCT Pub. No.: WO2014/108578
PCT Pub. Date: Jul. 17, 2014

(65) Prior Publication Data
US 2015/0306268 A1    Oct. 29, 2015

(51) Int. Cl.
*A61L 9/12* (2006.01)
*A61L 9/04* (2006.01)

(52) U.S. Cl.
CPC .. *A61L 9/12* (2013.01); *A61L 9/04* (2013.01)

(58) Field of Classification Search
CPC . Y10T 24/44017; Y10T 403/7176; A61L 9/12
(Continued)

(56) References Cited

U.S. PATENT DOCUMENTS

| | | | | |
|---|---|---|---|---|
| 168,972 | A * | 10/1875 | Dayton | A61L 9/12 128/207.14 |
| 3,252,580 | A * | 5/1966 | Getzin | B01D 25/26 210/485 |
| 3,784,102 | A * | 1/1974 | Stults | A01M 1/2055 239/36 |
| 3,964,684 | A * | 6/1976 | Schimanski | A61L 9/12 239/56 |
| 4,277,024 | A * | 7/1981 | Spector | A01M 29/12 206/466 |

(Continued)

FOREIGN PATENT DOCUMENTS

| ES | 1 050 301 U | 3/2002 |
|---|---|---|
| ES | 1 054 958 U | 9/2003 |

(Continued)

OTHER PUBLICATIONS

PCT International Preliminary Report (English Translation) dated Jul. 14, 2015 corresponding to PCT International Application No. PCT/ES2013/000008; 2 Pages (Patent Publication No. WO 2014/108578 A1).

(Continued)

*Primary Examiner* — Arthur O Hall
*Assistant Examiner* — Joseph A Greenlund
(74) *Attorney, Agent, or Firm* — Daly, Crowley Mofford & Durkee, LLP

(57) ABSTRACT

The air freshener consists of a small box formed by coupling together two parts (1, 2) in the form of box halves that can be tightly fitted together, with a perfume-impregnated cellulose block (5) between them. The cellulose block (5) is separated from the bottoms of the boxes and from the side walls by ledges (6) provided on the bottoms of both the female part (1) and the male part (2), and by partitions (7) provided on the male part (2), near the side walls thereof. The box has windows for air inlet (9) and for outlet (8) of the air impregnated with the perfume contained in the cellulose block (5). On the outside of the box there are conformations defining a dovetail joint (10) for securing a clip (11) which, when released from this mounting formed by the conformations (10), can be coupled to an outer recess in the bottom of the male part (2).

3 Claims, 3 Drawing Sheets

(58) Field of Classification Search
USPC .................................. 239/34–60, 8; 403/397
See application file for complete search history.

(56) References Cited

U.S. PATENT DOCUMENTS

| | | | | |
|---|---|---|---|---|
| 4,283,011 | A * | 8/1981 | Spector ................. | A01M 29/12 239/36 |
| 4,512,933 | A * | 4/1985 | Harden .................. | A61L 9/122 239/326 |
| 5,304,358 | A * | 4/1994 | Hoyt ........................ | A61L 9/12 239/56 |
| 5,422,078 | A * | 6/1995 | Colon ...................... | A61L 9/12 239/54 |
| 5,439,100 | A * | 8/1995 | Gordon .................... | A61L 9/12 206/204 |
| 5,468,447 | A * | 11/1995 | Bermas .................... | A61L 9/01 422/1 |
| 5,478,505 | A * | 12/1995 | McElfresh .............. | A61L 9/122 239/57 |
| 5,547,636 | A * | 8/1996 | Vick ....................... | A61L 9/042 239/60 |
| D384,408 | S * | 9/1997 | Foreman ................. | D23/366 |
| D403,420 | S * | 12/1998 | Vullion .................. | D11/81 |
| 5,865,372 | A * | 2/1999 | Ceresko ................... | A61L 9/03 239/60 |
| 5,899,382 | A * | 5/1999 | Hayes ..................... | A61L 9/12 239/56 |
| 6,746,521 | B2 * | 6/2004 | Canfield .................. | A61L 9/12 239/56 |
| 7,070,172 | B2 * | 7/2006 | Fabrega ............... | A01M 1/2033 239/59 |
| D555,778 | S * | 11/2007 | Fellows ................. | D23/366 |
| 7,887,760 | B2 * | 2/2011 | Yamamoto ........... | A01M 1/2033 422/124 |
| D709,172 | S * | 7/2014 | Brandenburg ........... | D23/366 |
| D715,915 | S * | 10/2014 | Schouten ................ | A61L 9/03 D23/368 |
| 9,205,163 | B2 * | 12/2015 | Westphal ................. | A61L 9/12 |
| 9,278,151 | B2 * | 3/2016 | Westphal ................. | A61L 9/12 |
| 2007/0051826 | A1 | 3/2007 | Schofield | |
| 2007/0057084 | A1 * | 3/2007 | Vieira ...................... | A61L 9/12 239/34 |
| 2007/0264169 | A1 * | 11/2007 | Chen ........................ | A61L 9/12 422/124 |
| 2008/0305016 | A1 * | 12/2008 | Fernandez Torres ..... | A61L 9/12 422/123 |
| 2013/0266486 | A1 * | 10/2013 | Wu .......................... | A61L 9/12 422/123 |
| 2014/0215772 | A1 * | 8/2014 | Ramsauer ............. | F16B 21/082 24/457 |
| 2015/0076246 | A1 * | 3/2015 | Bell ........................ | A61L 9/122 239/6 |
| 2015/0283883 | A1 * | 10/2015 | Schouten ............. | B60H 3/0028 239/57 |
| 2015/0306268 | A1 * | 10/2015 | Torres ...................... | A61L 9/12 239/57 |

FOREIGN PATENT DOCUMENTS

| | | |
|---|---|---|
| ES | 1 057 369 U | 7/2004 |
| ES | 1 063 656 U | 11/2006 |
| ES | 1 071 154 U | 1/2010 |
| FR | 2 611 456 A2 | 9/1988 |
| WO | WO 2014/108578 A1 | 7/2014 |

OTHER PUBLICATIONS

PCT Written Opinion of the ISA (English Translation) dated Sep. 16, 2013 corresponding to PCT International Application No. PCT/ES2013/000008; 5 Pages (Patent Publication No. WO 2014/108578 A1).

PCT International Search Report (with English Translation) dated Sep. 16, 2013 corresponding to International Application No. PCT/ES2013/000008; 7 Pages (Patent Publication No. WO 2014/108578 A1).

* cited by examiner

AIR FRESHENER

CROSS REFERENCE TO RELATED APPLICATION

This application is a U.S. National Stage of PCT application PCT/ES2013/000008 filed on Jan. 10, 2013, and entitled "AIR FRESHENER," which application is hereby incorporated herein by reference in its entirety.

OBJECT OF THE INVENTION

This invention relates to an air freshener, preferably and fundamentally intended for use in cars, although it may also be used in any other type of cabin in which its use is feasible.

The air freshener is embodied in a small box consisting of two box halves coupled together, one inside the other, with a perfume-impregnated cellulose block located between them.

The object of the invention is to obtain an air freshener with a simple structure, easy to use in the location in which it is placed.

BACKGROUND OF THE INVENTION

Spanish utility model U 200601878 describes a hanging box with an incorporated air freshener, consisting of two parts, one acting as a male part and the other acting as a female part, both fitting together, the male part being provided with a sort of internal peripheral groove into which a perimeter rim corresponding to the edge of male part is fitted, both being perfectly coupled together and conveniently retained, it being impossible for the box to be opened by small children.

Between the two constituent parts of the box, that is, between the male part and the female part, a perfume-impregnated cellulose block is located, in such a way as to enable the passage of air through windows provided in the lower part of the surface of the male part and in the upper part of the surface of the female part, with the perfume inside the box logically diffusing into the said air and exiting through the windows in the female part, perfuming the atmosphere.

This box is provided with a flap so that it may be hung via a suitable suspension element, being preferably and fundamentally intended for use in motor vehicles, with the box being hung from the internal rear view mirror, although with a suitable hanging device it could also be hung and used in other types of cabin.

The perfume-impregnated cellulose block requires a special configuration to allow air to pass through the inside of the box, the said cellulose block having wavy edges to allow the passage of air, also having a longitudinal groove along most of its length, to similarly facilitate the passage of air and for the said air to be impregnated with the perfume in the cellulose block, passing to the exterior through the windows in the box.

Obviously, producing a cellulose block with wavy edges and a longitudinal groove increases manufacturing costs.

Also, the box has no means of conveniently fixing the said cellulose block in place and it thus remains "loose" inside the box; in other words it is not conveniently adjusted inside the said box unless the block is of a considerable thickness, corresponding to the total depth of the box.

Another feature of the air freshener or box described in the said utility model U 200601878 is a tab located on the outer surface of both parts or box halves which may bear instructions for use, advertising, etc., the said tabs having a die-cast sector enabling this part to be withdrawn separately, uncovering the windows to allow air to enter and exit through them.

DESCRIPTION OF THE INVENTION

The proposed air freshener, although based on that referred to in the previous model, i.e. constituted of a small box formed by two box halves that can be coupled together, with air inlet and outlet windows, has a series of improvements and innovations simplifying the structure of the perfume-impregnated cellulose block, improving the immobilisation of the said cellulose block inside the box and improving the application of the air freshener with regard to its positioning in certain areas or parts of the vehicle.

More specifically, one of the features of the invention is that ledges are provided near the corners in both the bottom of the box half acting as the male part and the bottom of the box half acting as the female part, as a means of support for the perfume-impregnated cellulose block, the said block being separated from the said bottoms of the box to enable the air to circulate, with the consequent diffusion of the said air with the perfume impregnating the cellulose block.

Also, the bottom of the male part is provided with partitions near the side walls delimiting the space around the perimeter of the cellulose block, so that the said cellulose block is perfectly positioned in its location and cannot shift out of place, being blocked in all directions, i.e. around its perimeter, by the said partitions at the bottom of the male part.

Another innovative feature of the air freshener to which the invention relates is that both the box half acting as the male part and the box half acting as the female part have complementary protuberances on one of their shorter sides forming a dovetail joint on which, firstly, a sliding element is established for holding a clip in place to secure the air freshener unit, for example on the corresponding vehicle dashboard air outlet grille, for which purpose the said clip, on being used, must be released from the dovetail joint and fitted by means of a stud on the base of the clip into a specially configured recess for this purpose on the outer surface of the box half acting as the male part, the said recess creating a peripheral opening around the inside, and also having two sections of different widths, to house the constricted stud on the clip and to fix the box unit to this clip, and so that the said clip can be fixed to a vehicle dashboard grille, as already mentioned.

The tab for covering the outer surface of the aforementioned male part has a die-cast area which can be moved in such a way as to uncover the air intake windows, the said tab extending to a sector that also conceals the aforementioned die-cast area, so that withdrawing the said die-cast area firstly uncovers the air intake windows and secondly releases the die-cast area to allow the clip to be mounted and fixed to the box.

The aforementioned features make the air freshener more practical, with regard to both the embodiment of the cellulose block and the application or arrangement of the box to which the invention relates, in any location, as the box described in the background of the invention in the utility model cannot be used on a vehicle dashboard grille, while the air freshener to which the invention relates can be used on the said vehicle dashboard grille, increasing the intensity of the perfume as a result of the air flowing out of the said dashboard grille.

DESCRIPTION OF THE DRAWINGS

To complement the current description and to facilitate a better understanding of the features of the invention, a drawing is attached as an integral part of this description, in which the following is shown, with an illustrative and non-limiting character.

PREFERRED EMBODIMENT OF THE INVENTION

Figure 1:
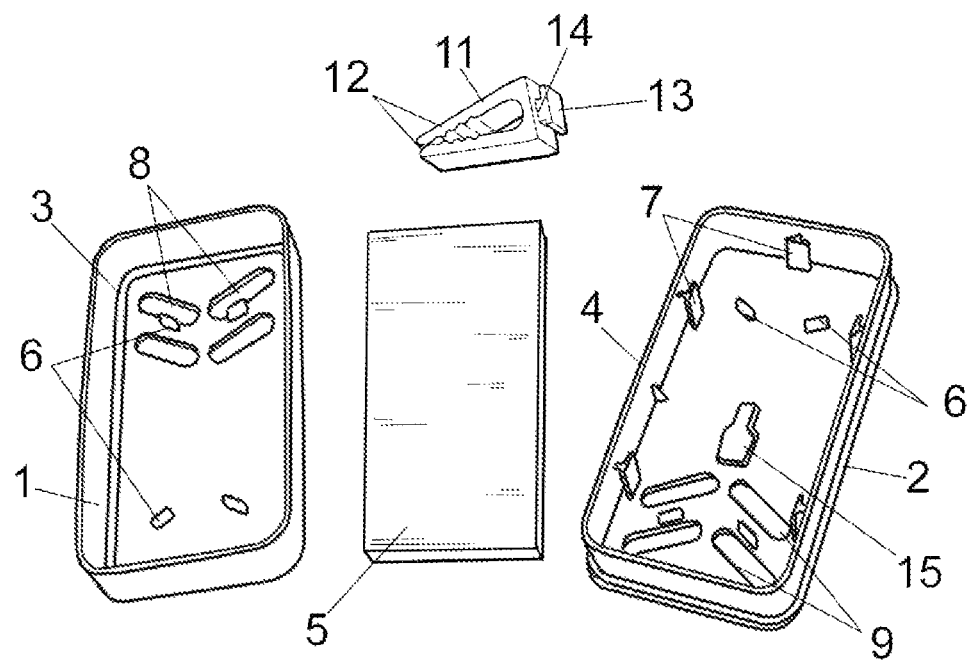
FIG. 1.—Shows an exploded diagram of the three parts constituting the air freshener to which the invention relates, whose parts correspond to the two box halves that can be coupled together and the perfumed cellulose block.
Figure 2:
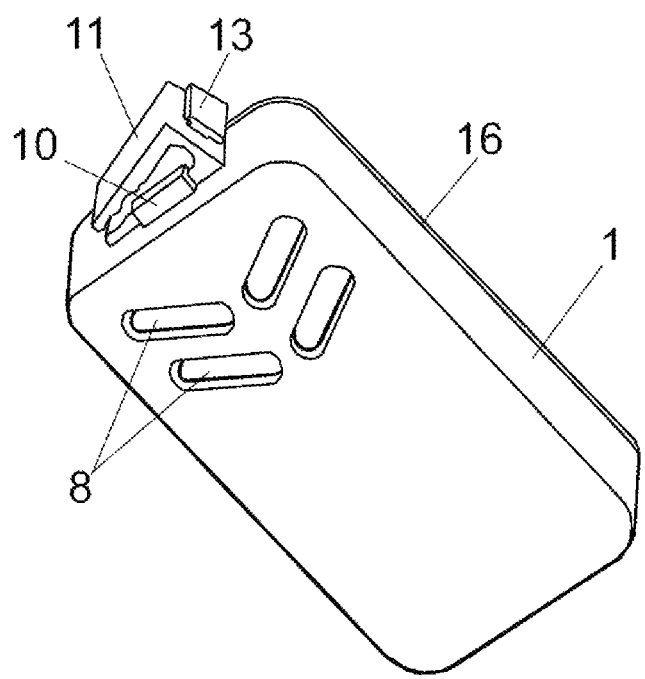
FIG. 2.—Shows a perspective view of the air freshener to which the invention relates, including its fixing clip, the view corresponding to the outer surface of the female part.
Figure 3:
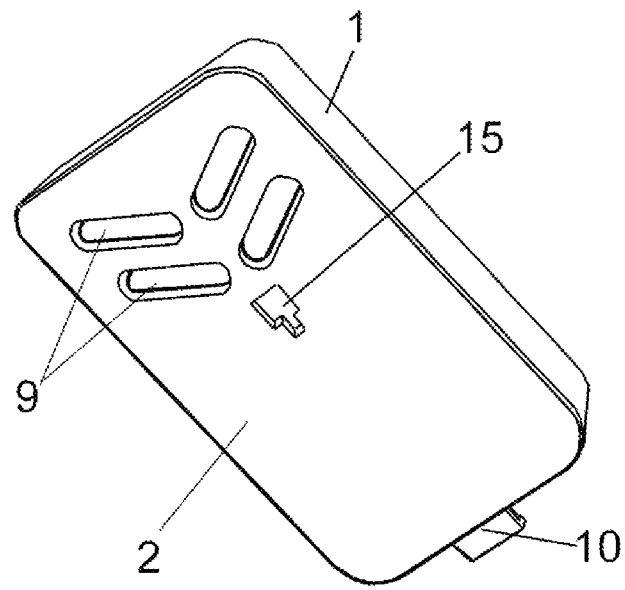
FIG. 3.—Shows another perspective view, in this case of the outer surface of the male part, corresponding to the air freshener shown in FIG. 2, but without the clip.
Figure 4:
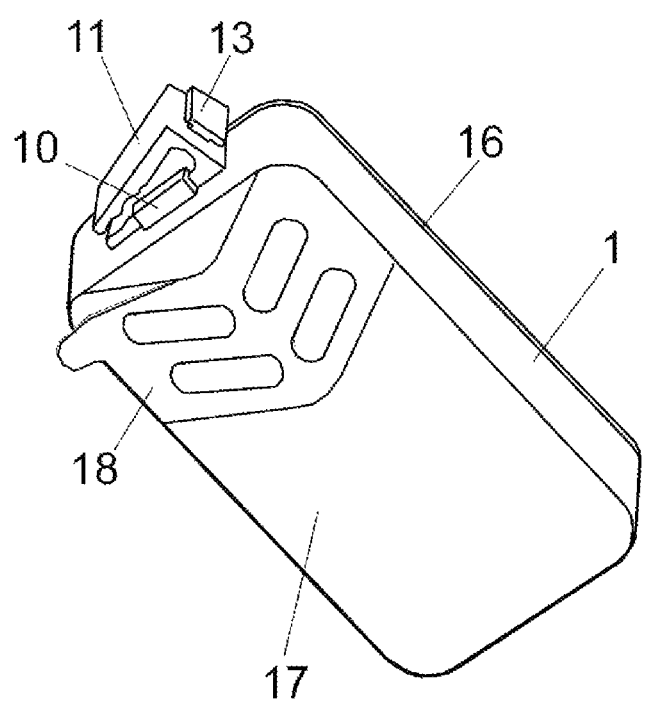
FIG. 4.—Shows a perspective view similar to that of FIG. 2, with the die-cast tab covering the air outlet windows.
Figure 5:
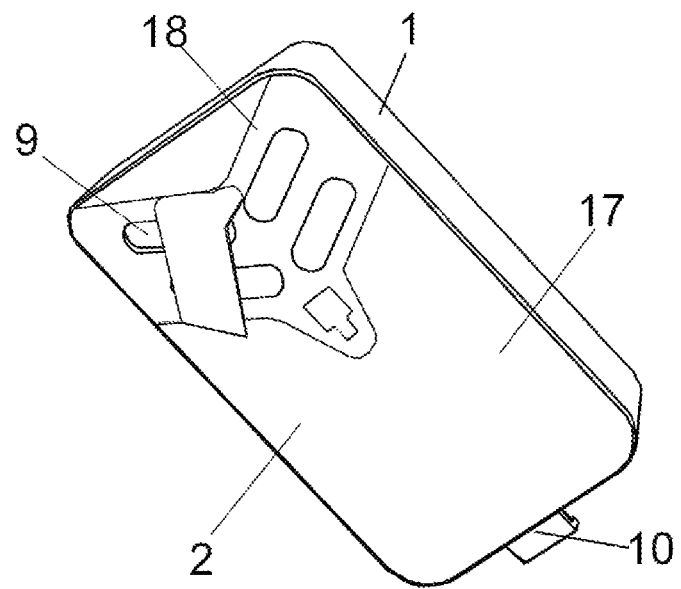
FIG. 5.—Shows the same view as that of FIG. 3, with the tab covering the windows and with the die-cast area for mounting the air freshener fixing clip.
Figure 6:
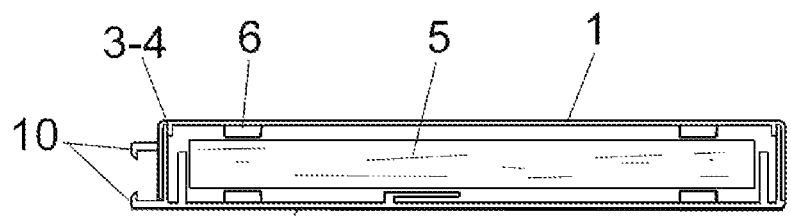
FIGS. 6 and 7.—Show the respective longitudinal and transverse section views of the air freshener to which the invention relates.
Figure 7:
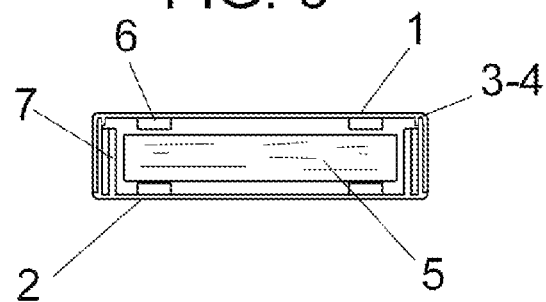

As can be seen in the aforementioned figures, the air freshener to which the invention relates is constituted by two parts in the form of box halves (1, 2) which can be tightly fitted into each other, with part (1) acting as the female part and part (2) acting as the male part, that is, the latter fits tightly into the former.

The female part (1) has a narrow groove (3) around its entire base perimeter, for fitting and coupling a perimeter rim (4) corresponding to the male part (2), so that the two parts (1, 2) fit perfectly together and it would be impossible for a small child to separate them.

The box constituted by the said parts (1, 2) contains a perfume-impregnated cellulose block (5), this cellulose block (5) being separated from the bottoms of the parts (1, 2) by means of ledges (6) on the said bottoms of the parts, close to the corners, so that the said cellulose block (5), resting on the ledges (6) of both parts (1, 2), is separated from the bottom of the parts, allowing the passage of air.

Also, this cellulose block (5) is separated from the side walls, the male part (2) being provided with partitions (7) near its side walls protruding from the bottom of the part itself, precisely delimiting the profile of the cellulose block (5), the cellulose block fitting perfectly between the said partitions (7) and being immobilised between them and the ledges (6) on the bottoms of the parts (1, 2).

There are air outlet windows (8) on the bottom of the female part (1), while on the bottom of the male part (2) there are also windows (9), but these are located opposite the air outlet windows (8), that is, in the lower part, so that the air can enter the lower windows (9) of the male part (2), flow through the inside of the box and exit the box via the upper windows (8) of the female part (1), thus diffusing the perfume into the atmosphere, carried by the air flowing through the inside of the box.

At each end of both parts (1, 2), there are conformations (10) which can be fitted to one of the side arms of a clip (11) provided with indentations (12) on both arms for fixing or securing to a vehicle dashboard air outlet grille, for example, and whose clip (11) has a stud (13) on its base, protruding from a constriction (14) as a part between the stud (13) and the base of the said clip (11).

Before use, the said clip (11) with which the air freshener is provided will be retained on the support constituted by the dovetail formed by the two complementary parts (10) of the female part (1) and the male part (2), while the clip (11) will be released from this support when it is about to be used, and its stud (13) will be used to fit it into an outer recess (15) in the bottom of the male part (2), the said recess opening onto the inside and also consisting of two sections, one for housing the stud (13) on the clip (11) and enabling it to slide, and the other for retaining the said stud (13) via the constricted section (14) which is housed in the narrower section of the said recess (15).

Also, the base or bottom of the male part (2) has a perimeter rim (16) limiting the depth of penetration when it is fitted into the female part (1).

Finally, the outer surface corresponding to the bottom of the female part (1) and the bottom of the male part (2) is provided with tabs (17) on which an advertising message or instructions for use may be printed, the said tags being provided with a die-cast section delimiting sectors (18) for covering the windows (8, 9) of the said male part (2) and female part (1), these sectors being withdrawable to uncover the window and allow air to flow from the outside to the inside and from the inside to the outside, through the aforementioned windows, the die-cast area of the tab corresponding to the outer surface of the male part (2) also covering the recess (15) in the said bottom of this part.

The invention claimed is:

1. An air freshener comprising:
a box formed by tightly coupling together two parts in the form of box halves, the first acting as a female part and the second as a male part, containing a cellulose block impregnated with a perfume which is diffused to the outside air by impregnation of the air entering windows provided in the lower part of the bottom of the male part and exiting through windows provided in the upper part of the bottom of the female part, the parts being provided with means for coupling and retaining so that the box and the perfume-impregnated cellulose block inside it remain intact,
wherein both the bottom of the female part and the bottom of the male part are provided with internal ledges near the corners as supports for the cellulose block, the cellulose block being separated from the bottom of both parts of the box formed by the female and male parts; partitions have also been provided, protruding from the bottom of the male part near its walls and parallel to the same, delimiting a space for location and immobilization of the cellulose block, which, in combination with the ledges on the bottoms of the parts, enables the free circulation of the air inside the box and diffusion of the perfume impregnating the cellulose block; opposing protrusions have also been provided on the outside of one of the shorter sides of the male part and of the female part, constituting a joint as a mounting for a clip that can be fitted into a recess provided on the outside of the bottom of the male part; and
wherein the clip is formed by two converging arms, with indentations between them for purposes of fixing, there being a stud on the base of the clip with a constriction for separating the stud from the base of the clip, so that the clip may be fitted into the recess on the outside of the bottom of the male part, using the stud.

2. The air freshener of claim 1, wherein the recess on the bottom of the male part has two sections of different widths, for insertion of the stud located on the clip, for sliding and fixing the clip to the narrower section of the outer recess.

3. The air freshener of claim 2, wherein outer surfaces of the bottom of the male part and the female part are provided with respective tabs for covering the windows provided in the female part and male part, with the particularity of the tabs having a die-cast area that can be withdrawn to uncover the corresponding windows, the die-cast area extending along the tab located on the outer surface of the bottom of the male part, being of a suitable width to cover and obstruct the outer recess for mounting the clip.

* * * * *